United States Patent [19]

Shibatani et al.

[11] Patent Number: 5,208,156
[45] Date of Patent: May 4, 1993

[54] ESTERASE PURIFIED FROM SERRATIA MARCESCENS SR41 (FERM BP-NO. 487)

[75] Inventors: Takeji Shibatani; Hiroaki Matsumae, both of Kobe; Hiroyuki Akatsuka, Osaka, all of Japan

[73] Assignee: Tanabe Seiyaku Co., Ltd., Osaka, Japan

[21] Appl. No.: 668,979

[22] Filed: Mar. 12, 1991

[30] Foreign Application Priority Data

Mar. 13, 1990 [JP] Japan .................................. 2-63830

[51] Int. Cl.$^5$ ........................... C12N 9/16; C12N 1/00
[52] U.S. Cl. ..................................... 435/196; 435/881
[58] Field of Search ................................ 435/881, 196

[56] References Cited

FOREIGN PATENT DOCUMENTS 0362556 4/1990 European Pat. Off. .
57-177696 11/1982 Japan .
61-280296 12/1986 Japan .
1-181788 7/1989 Japan .

OTHER PUBLICATIONS

Goullet, J. Gen. Microbiol., 1978, 108/2, 275–281.
Mathur et al., J. Environ. Qual., 1975, 4/2, 273–275.
Decedue et al., Biochim. Biophys. Acta., 569(2), 293–301, 1979.
Goullet, C. R., Hebd. Seances Acad. Sci., Paris, Ser. D; 287(4), 383–5, 1978.
Hines et al., J. Bacteriology, vol. 170, 1559, 1988, 4141–46.
Camarillo et al., Rev. Latinoamer. Microbiol., 1972, 14(1), 29–35.
Picard et al., J. Hosp. Infect., 11(2), 1988, 194–5.
Dymshits et al., Mol. Biol. 11 (3 part 1), 1977, 405–9.
Andreev et al., Mikrobiologiya, 45(1), 1976, 157–60.
Bohne et al., Zentvalbl Bakteriol Parasitenkd, Dr. Fektianskr Hyg Erste Abtorig Reine a Med Mikrobiol Parasitol, 228 (1/2), 1974, 117.
Okabayashi et al., Biochim. Biophys. Acta., 220(1), 1970, 116–123.
Unemoto, Annu. Rep. Inst. Food Microbiol Chiba Univ., 21, 1968, 87–97.
Matsunaga et al., Archives of Biochemistry and Biophysics, vol. 160, pp. 504–513 (1974).
Tsujisaka et al., Agr. Biol. Chem., vol. 37, pp. 1457–1464 (1973).
Ohkawa et al., J. Biochem., vol. 86, pp. 643–656 (1979).
Nakagawa et al., J. Biochem., vol. 95, pp. 1047–1054 (1984).
Chemical Abstracts, vol. 93, No. 9, Bashkatova et al., "Isolation and characterization of intracellular lipase from Serratia marcescens 345".

Primary Examiner—David M. Naff
Assistant Examiner—Mike Meller
Attorney, Agent, or Firm—Birch, Stewart, Kolasch & Birch

[57] ABSTRACT

A novel esterase which is derived from Serratia marcescens is disclosed. Said esterase has the following physico-chemical properties and enzymatic characteristics:

(1) Activity; it (i.e., said esterase) hydrolyzes an ester bond of organic carboxylates, (2) Substrate specificity; it acts on alkyl esters of organic carboxylic acids, triglycerides or thiol esters, (3) Optimum pH; its optimum pH is 7.5–9.0 when the hydrolysis is carried out by using olive oil as the substrate, (4) pH stability; it is stable at pH 5.0–9.0 when it is stored at 30° C. for one hour, (5) Optimum temperature; its optimum temperature is 40°–50° C. when the hydrolysis is carried out by using olive oil as the substrate, (6) Heat stability; it is stable at a temperature of not higher than 50° C. when it is stored at pH 8.0 for 30 minutes, (7) Molecular weight; 62,000±2,000 (SDS-polyacrylamide gel electrophoresis), (8) Isoelectric point; 4.6±0.1, (9) Effect of metal ions; it is activated in the presence of 1 mM calcium ion, and inhibited in the presence of 1 mM cobalt ion, nickel ion, iron ion or ethylenediamine-tetraacetic acid. Said esterase can widely be applied for organic synthetic reactions.

1 Claim, No Drawings

ESTERASE PURIFIED FROM SERRATIA MARCESCENS SR41 (FERM BP-NO. 487)

BACKGROUND OF THE INVENTION

1. Field of the Invention

This invention relates to novel esterase and process for preparing the same.

2. Description of Related Art

Recently, attempts have been made to use esterase for organic synthetic reactions (e.g., hydrolysis reaction). For example, esterase derived from pig liver is often used for this purpose. However, this esterase is disadvantageous for industrial use because it is expensive. On the other hand, there have been known esterases derived from microorganisms such as *Arthrobacter globiformis* IFO 12985 [Patent Publication (unexamined) No. 181788/1989] (Molecular Weight: 43,000), *Bacillus stearothermophilus* [Archiv. Biochem. Biophys. 160, 504–513 (1974)] (Molecular Weight: 47,000), *Geotrichum candidum* [Agric. Biol. Chem. 37 (6), 1457–1464 (1973)] (Molecular Weight: 53,000–55,000), *Pseudomonas aeruginosa* [J. Biochem. 86, 643–656 (1979)] (Molecular Weight: 55,000), *Pseudomonas fluorescens* [J. Biochem. 95, 1047–1054 (1984)] (Molecular Weight: 48,000). However, these esterases have difficulties that they can not be widely applied because of their narrow substrate specificities.

SUMMARY OF THE INVENTION

The object of the present invention is to provide a novel esterase which is derived from a microorganism and can be applied for organic synthetic reactions as widely as pig liver esterase.

A further object of the present invention is to provide a process for preparing said esterase.

Another object of the present invention is to provide a process for preparing a lower alkyl (2R, 3S)-3-(4-lower alkoxyphenyl)glycidate by using said esterase.

As a result of various investigations, we have now found a potent esterase which is derived from a microorganism belonging to the genus *Serratia*.

DETAILED DESCRIPTION OF THE INVENTION

The esterase of the present invention is a novel esterase having the following physico-chemical properties and enzymatic characteristics:

(1) Activity

It (i.e., said esterase) hydrolyzes an ester bond of an organic carboxylates.

(2) Substrate specificity

It acts on alkyl esters of organic carboxylic acids, triglycerides or thiol esters. For example, the esterase of the present invention has ability to hydrolyze a lower or higher alkyl esters of organic carboxylic acids (e.g., a lower fatty acid, a higher fatty acid, a lower alkoxy-substituted-phenylglycidic acid and the like). Moreover, it also has potent ability to hydrolyze triglycerides composed of glycerol and water-soluble lower fatty acids or water-soluble higher fatty acids. Further, it also has ability to hydrolyze thiol esters such as dimercaprol tributyrate and the like. But it has no ability to hydrolyze casein.

(3) Optimum pH

It shows optimum pH of about 7.5–9.0 when olive oil is used as the substrate.

(4) pH stability

It remains more than 95% of its activity when it is stored at a pH 5–9 at 30° C. for 60 minutes.

(5) Optimum temperature

It shows optimum temperature of about 40°–50° C. when the enzymatic reaction is carried out in 100 mM Tris-HCl buffer (pH 8.0) by using olive oil as the substrate.

(6) Heat stability

It retains 100% of its activity when it is stored at a temperature not higher than 50° C. in 100 mM Tris-HCl buffer (pH 8.0) for 30 minutes.

(7) Assay of enzyme activity (a) activity on olive oil

The enzyme reaction is carried out at pH 8.0 at 37° C. for 20 minutes by using olive oil as the substrate. The activity of the esterase which produces one $\mu$ mole of fatty acid per minute is defined as one unit. (cf., Example 1)

(b) activity on triglycerides or fatty acid esters

The enzyme reaction is carried out at pH 8.0 at 37° C. for 10 minutes by using triglycerides or fatty acid esters as the substrate. The activity of the esterase which produces one $\mu$ mole of fatty acid per minute is defined as one unit.

(c) activity on thiol esters

The enzyme reaction is carried out at pH 8.5 at 30° C. for 10 minutes by using dimercaprol tributylate as the substrate. After the reaction, 5,5'-dithiobis(2-nitrobenzoic acid) (color-producing reagent) is added to the reaction mixture. The amount of the liberated 5-mercapto-2-nitrobenzoic acid is measured by spectrophotometer. The activity of the esterase which produces one $\mu$ mole of 5-mercapto-2-nitrobenzoic acid per minute is defined as one unit. (cf., Example 4)

(8) Molecular weight 62,000±2,000 (SDS-polyacrylamide gel electrophoresis)

(9) Isoelectric point 4.6±0.1

(10) Effect of metal ions

It is activated in the presence of 1 mM calcium ion. On the other hand, its activity is inhibited by 40–90% in the presence of 1 mM zinc ion, copper ion, manganese ion, and completely inhibited in the presence of 1 mM cobalt ion, nickel ion, iron (II) ion, iron (III) ion or ethylenediaminetetraacetic acid.

The above-mentioned esterase of the present invention is obviously different from known esterases in that it has molecular weight of 62,000±2,000 (measured by SDS-polyacrylamide gel electrophoresis) and isoelectric point of 4.6±0.1.

According to the present invention, the above-mentioned esterase can be prepared by cultivating a microorganism belonging to the genus Serratia in a medium, accumulating said esterase inside or outside of the microorganism, and recovering the accumulated esterase therefrom.

Any microorganism belonging to the genus Serratia which can produce the above-mentioned esterase may be used as the esterase-producing microorganism of the present invention. Examples of such microorganism include *Serratia marcescens* Sr41 (FERM-BP No. 487), a mutant thereof and the like. But, the microorganism used in the present invention are not limited to those mentioned-above. For example, a recombinant which is produced from the above mentioned microorganisms according to the bioengineering methods may be also used.

Any medium in which the esterase-producing microorganisms of the present invention can grow and proliferate may be used as the medium. Examples of the carbon source include, for example, sugars such as glucose, sucrose, molasses and the like, organic acids such as fumaric acid, citric acid and the like, alcohols such as glycerol and the like, amino acids such as alanine, glutamine, asparagine and the like and so forth. Inorganic ammonium salts such as ammonium sulfate, ammonium chloride and the like, urea, peptone, corn steep liquor, yeast extract, casein hydrolysate and the like can be used as the nitrogen source. It is preferred to use 1-15 w/w % of the carbon source and 0.1-2.0 w/w % of the nitrogen source. If required, inorganic salts such as phosphates, magnesium salts, potassium salts, calcium salts and the like, or metal ions such as iron ions, manganese ions, copper ions, zinc ions and the like may be added to the medium. When a synthetic medium is used, vitamins such as biotin, thiamin and the like, or growth-promoting substances such as carnitine may, if required, be added to the medium. Moreover, inducers such as vegetable oils or surfactants may, if necessary, be added to the medium. It is preferred to adjust the pH of the medium to a pH of about 5-8.

The cultivation can be carried out in a conventional manner after inoculating the microorganism into the medium. For example, any method such as shake culture, aeration spinner culture, stationary culture or continuous culture may be used for this purpose.

The condition of cultivation may vary depending on a kind of the medium, a cultivation method and the like. Any condition under which the microorganism of the present invention can grow, proliferate and produce the esterase is appropriate for this purpose. But it is usually preferred to begin the cultivation at a pH of about 5-8, and then carry it out at room temperature or under warming, for example, at a temperature between 20° and 40° C. for one to 2 days.

The esterase accumulated inside or outside of the cultivated microorganism can be recovered and purified in a conventional manner. For example, the esterase accumulated in the culture broth can be recovered by a combination of known methods such as salting-out with inorganic salt (e.g., ammonium sulfate, an alkali metal sulfate or an alkali metal halide), differential precipitation with hydrophilic organic solvent (e.g., an alcohol or acetone), column chromatography by ion exchange resin or hydrophobic resin, gel filtration and protein precipitation with nucleic acid, tannin or the like. The thus-obtained esterase can be further purified by a combination of known purification methods such as isoelectric precipitation, dialysis, electrodialysis, electrophoresis and the like. For example, the purification is carried out by;

(1) removing microbial cells from the culture broth by centrifugation, (2) treating the supernatant with a 45% saturated ammonium sulfate solution, (3) subjecting the resulting precipitate to an anion exchange resin (DEAE-TOYOPEARL 650M, MonoQ) chromatography after dialysis thereof, (4) subjecting active fractions to hydrophobic resin (Butyl-TOYOPEARL 650S) chromatography after dialysis thereof, and (5) subjecting the obtained active fractions to gel filtration (Superose 6) after dialysis and condensation thereof. The thus-obtained purified esterase is a polypeptide showing a single band with a molecular weight of $62,000 \pm 2,000$ by SDS-polyacrylamide gel electrophoresis.

As mentioned before, the esterase of the present invention has a potent ability to hydrolyze a wide range of substrates such as alkyl esters of organic carboxylic acids, triglycerides or thiol esters. Therefore, it can be applied for organic synthetic reactions as widely as pig liver esterase. For example, it can be applied for preparation of an optically active isomer from a racemic mixture thereof, or preparation of a chiral compound from a prochiral compound thereof. In particular, the esterase of the present invention is characterized in that it has strong ability to hydrolyze a (lower)alkyl (lower)alkoxyphenylglycidate. For example, when it is used for hydrolysis of a racemic lower alkyl trans-3-(4-lower alkoxyphenyl)glycidate, a lower alkyl (2R, 3S)-3-(4-lower alkoxyphenyl)glycidate can be prepared in good yield. The thus-obtained lower alkyl (2R, 3S)-3-(4-lower alkoxyphenyl)glycidate is useful as a synthetic intermediate of pharmaceuticals such as diltiazem hydrochloride.

In the following Examples, "%" means "w/v%" unless otherwise prescribed.

EXAMPLES

EXAMPLE 1

A medium (pH 7.0, 20 liters) containing dextrin (1%), ammonium sulfate (0.2%), meast-S (2%), potassium dihydrogenphosphate (0.1%), magnesium sulfate (0.05%), calcium chloride (0.01%), ferrous sulfate (0.001%), Tween80 (0.5 v/v%) and polyalkylene glycol derivative-type surfactant (trade name: KARARIN 102, manufactured by Sanyo Chemical Industries, Ltd., 0.1 v/v%) was placed in a 30-liter jar-fermenter and sterilized by autoclaving. A broth (200 ml) of *Serratia marcescens* Sr 41 which was obtained by reciprocal shaking at 30° C. for 20 hours in the same medium as above was inoculated into the sterilized medium. The cultivations was carried out by aeration and agitation (200 rpm, 0.5 vvm) at 30° C. for 18 hours. The culture broth was centrifuged, and the supernatant (4.5 liters) was salted out with 45% saturated ammonium sulfate solution. The precipitate was collected by filtration with celite, eluted with water. The eluate was dialyzed and lyophilized. 4.1 g of esterase (18,600 unit/g) were obtained as crude enzyme powder.

(Assay of enzyme activity)

The enzyme activity was estimated according to the following method.

A mixture of 225 ml of 2% polyvinyl alcohol (Poval 117, manufactured by Kurare Co., Ltd.) and 75 ml of olive oil was emulsified by stirring at 14,500 rpm at 5°-10° C. for 10 minutes. 5.0 ml of the olive oil-emulsion thus-obtained and 4.0 ml of 0.25M Tris-HCl buffer (pH 8.0, containing 2.5 mM calcium chloride) were preincubated at 37° C. for 10 minutes. One ml of an enzyme solution was added thereto to initiate enzymatic reaction. After the mixture was incubated at 37° C. for 20 minutes, 20 ml of a mixture of acetone-ethanol (1:1) were added to the reaction mixture to stop the enzymatic reaction. The mixture was titrated with 0.05N sodium hydroxide solution by using phenolphthalein as the indicator. A blank solution was prepared in the same manner as above except that acetone-ethanol (1:1) is added to the substrate solution before addition of the enzyme solution. Said blank solution was titrated in the same manner as above. The amount of enzyme which liberated one μmole of fatty acid per minute was defined as one unit (U).

EXAMPLE 2

10 liters of the supernatant obtained in the same manner as described in Example 1 were salted out with 45% saturated ammonium sulfate solution. The precipitate (esterase) was dissolved in 20 mM Tris-HCl buffer (pH 7.5). The solution was dialyzed and subjected to a column of an anion exchange resin (DEAE-TOYOPEARL 650M, Toyo Soda Co., Ltd.) which was pre-equilibrated with the same buffer. The column was washed with 20 mM Tris-HCl buffer (pH 7.5). The elution of enzyme was carried out by a liner gradient of 0 to 1.0M sodium chloride solution containing 20 mM Tris-HCl buffer (pH 7.5). Esterase was eluted with about 0.27M sodium chloride solutions containing 20 mM Tris-HCl buffer (pH 7.5). The active fractions were collected and dialyzed against 20 mM Tris-HCl buffer (pH 7.5) and subjected to a column of a strong anion exchange resin (MonoQ, manufactured by Pharmacia LKB Biotechnology) which was pre-equilibrated with the same buffer. The column was washed with 20 mM Tris-HCl buffer (pH 7.5). The elution of enzyme was carried out by a liner gradient of 0 to 0.6M sodium chloride solutions containing 20 mM Tris-HCl buffer (pH 7.5). Esterase was eluted with about 0.35M sodium chloride solutions containing 20 mM Tris-HCl buffer (pH 7.5). The active fractions were collected and dialyzed against 5% saturated ammonium sulfate solution containing 20 mM Tris-HCl buffer (pH 7.5) and subjected to a column of a hydrophobic resin (Butyl-TOYOPEAL 650S, manufactured by Toyo Soda Co. Ltd.) which was pre-equilibrated with the same buffer. The column was washed with the same buffer (pH 7.5). The elution of enzyme was carried out by a liner gradient of 5 to 0% saturated ammonium sulfate solution containing 20 mM Tris-HCl buffer (pH 7.5). The active fractions were collected and dialyzed against 0.15M sodium chloride solution containing 20 mM Tris-HCl buffer (pH 7.5) and condensed. The residue was subjected to gel filtration of molecular sieve resin (Superose 6, manufactured by Pharmacia LKB Biotechnology) which was pre-equilibrated with the same buffer. 56.8 mg of purified esterase protein were obtained.

The purified esterase showed molecular weight of about 590,000 by gel filtration and about 62,000 by SDS-polyacrylamide gel electrophoresis.

The specific activities and yields of esterases obtained in each of the above purification steps are shown in the following Table 1. (The enzyme activity was estimated in the same manner as described in Example 1 and the amount of protein was measured by Lowry method.)

The esterase obtained above showed no protease activity when casein was used as the substrate.

TABLE 1

| Purification step | Total protein (mg) | Total activity (units) | Specific activity (units/mg protein) | Yield (%) |
| --- | --- | --- | --- | --- |
| Supernatant of culture | 16470 | 385400 | 23.4 | 100 |
| 45% ammonium sulfate | 1529 | 341000 | 223 | 88.5 |
| DEAE-TOYOPEAL 650M | 247 | 227500 | 921 | 59.0 |
| MonoQ | 143 | 141300 | 988 | 36.7 |
| Butyl-TOYOPEAL 650S | 84.5 | 85350 | 1010 | 22.1 |
| Superose 6 | 56.8 | 58500 | 1030 | 15.2 |

EXAMPLE 3

The substrate specificity on various kinds of triglycerides and fatty acid esters was investigated with respect to the esterase obtained in Example 2.

Assay of hydrolyzing activity on triglycerides and fatty acid esters 0.2 g of each substrate, 4 ml of 0.2M Tris-HCl buffer (pH 8.0) and one ml of 6 mM calcium chloride solution were placed in 100 flask. After a ten minute-preincubation, one ml of enzyme solution was added thereto to initiate enzymatic reaction. The mixture was incubated at 37° C. under 80 rpm for 10 minutes. 20 ml of a mixture of acetone-ethanol (1:1) were added to the reaction mixture to stop the enzymatic reaction. The mixture was titrated with 0.05N sodium hydroxide solution by using phenolphthalein as the indicator. A blank solution was prepared in the same manner as above except that acetone-ethanol (1:1) was added to the substrate solution before addition of the enzyme solution. Said blank solution was titrated in the same manner as above. The amount of enzyme which can liberate one μmole of fatty acid per minute is defined as one unit. (Results)

The result are shown in the following Tables 2 and 3. The enzyme activity is shown as relative activity (%) [methyl n-caprylate (Table 2), tricaprylin (Table 3)=100].

TABLE 2

| Substrate | Relative activity (%) |
| --- | --- |
| methyl acetate | 9.7 |
| methyl n-butyrate | 72.8 |
| methyl n-valerate | 38.9 |
| methyl n-caproate | 14.6 |
| methyl n-caprylate | 100[1] |
| methyl n-caprate | 92.2 |
| methyl laurate | 61.2 |
| methyl myristate | 34.0 |
| methyl palmitate | 14.6 |
| methyl linolenate | 38.9 |
| methyl linolate | 51.5 |
| methyl oleate | 2.9 |

[1] 204 unit/mg protein

TABLE 3

| Substrate | Relative activity (%) |
| --- | --- |
| triacetin | 7.6 |
| tributylin | 93.2 |
| tricaproin | 70.3 |
| tricaprylin | 100[2] |
| tricaprin | 42.4 |
| trilaurin | 29.7 |
| trimyristin | 33.9 |
| tripalmitin | 1.6 |
| Tristearin | 1.6 |

[2] 1169 unit/mg protein

EXAMPLE 4

The substrate specificity on dimercaprol tributyrate was investigated with respect to the purified esterase obtained in Example 2.

The esterase was added to a substrate solution of Lipase Kit S [Substrate: dimercaprol tributyrate, manufactured by Dainippon Pharmaceutical Co., Ltd.]. After the hydrolysis was carried out, 5,5-dithiobis(2-nitrobenzoic acid) (color-producing agent) was added to the reaction mixture. Enzyme activity was estimated by measuring the amount of the liberated 5-mercapto-2-nitrobenzoic acid at 412 nm.

The esterase showed the enzyme activity of $1.7 \times 10^5$ units/mg protein.

EXAMPLE 5

1.5 mg of the purified esterase obtained in Example 2 were added to 75 ml of an aqueous 1 mM calcium chloride solution. 75 ml of toluene solution containing 1M racemic methyl trans-3-(4-methoxyphenyl)glycidate were added thereto. The mixture was adjusted to pH 8.0 and stirred at 30° C. for 4 hours. After the reaction, the ratio of (+)-isomer [(2S, 3R)-isomer] and (−)-isomer [(2R, 3S)-isomer] of methyl trans-3-(4-methoxyphenyl)glycidate in toluene layer was measured by High Performance Liquid Chromatography (column: Chiralcel OJ, manufactured by Daicel Chemical Industries, Ltd., mobile phase: n-hexane:isopropyl alcohol=9:1).

The results are shown in the following Table 4

TABLE 4

| The ratio of optically active isomers (%) | | Optical yield of (−)-trans-isomer (%) |
|---|---|---|
| (+)-trans-isomer | (−)-trans-isomer | |
| 0.4 | 99.6 | 94 |

EXAMPLE 6

Optimum pH and pH stability were investigated with respect to the purified esterase obtained in Example 2.

Optimum pH was determined by measuring the enzyme activity in the same manner as described in Example 1 except that the enzymatic reaction was carried out at various pH. The each activity was shown as relative activity (%) (the activity at pH 8=100).

On the other hand, pH stability was examined by adjusting the enzyme solution at a specified pH, incubating at 30° C. for one hour and then estimating the enzyme activity in the same manner as described in Example 1. The enzyme activity was shown as the relative activity (%) of residual activity (the activity measured immediately before incubation=100), and the pH adjustment was carried out by using McIlvaine buffer (pH 3.0-7.0), 100 mM Tris-HCl buffer (pH 8.0-9.0) and 100 mM glycine buffer (pH 9.0-11.0).

(Results)

The results are shown in the following Table 5 and 6. It is clear from these Tables that the optimum pH of the esterase is about 7.5-9.0, and the esterase is stable at a pH of about 5-9.

TABLE 5

| pH | 3 | 4 | 5 | 6 | 7 | 8 | 9 | 10 | 11 |
|---|---|---|---|---|---|---|---|---|---|
| (Relative activities at each pH) | | | | | | | | | |
| Relative activity (%) | 0 | 5 | 20 | 39 | 69 | 100 | 80 | 2 | 0 |

TABLE 5-continued

| pH | 3 | 4 | 5 | 6 | 7 | 8 | 9 | 10 | 11 |
|---|---|---|---|---|---|---|---|---|---|
| (Relative activities at each pH) | | | | | | | | | |
| (%) | | | | | | | | | |

TABLE 6

| pH | 3 | 4 | 5 | 6 | 7 | 8 | 9 | 10 | 11 |
|---|---|---|---|---|---|---|---|---|---|
| (pH stability) | | | | | | | | | |
| Residual activity (%) | 0 | 5 | 95 | 100 | 100 | 100 | 100 | 65 | 0 |

EXAMPLE 7

Optimum temperature and heat stability were investigated with respect to the purified esterase obtained in Example 2.

The optimum temperature was determined by measuring the enzyme activity in the same manner as described in Example 1 except that the enzymatic reaction is carried out at various temperature. The enzyme activity was shown as relative activity (%) (the activity at 45° C.=100).

On the other hand, the heat stability was examined by incubating the enzyme in 100 mM Tris-HCl buffer for 30 minutes at a specified temperature, and estimating the enzyme activity in the same manner as described in Example 1. The enzyme activity was shown as the relative activity (%) of residual activity (the activity measured immediately before incubation=100).

(Results)

The results are shown in the following Table 7 and 8. It is clear from Tables that the optimum temperature is about 40° to 50° C., and the esterase is stable at a temperature not higher than 50° C.

TABLE 7

| Temperature (°C.) | 10 | 15 | 20 | 30 | 35 | 40 | 45 | 50 | 55 |
|---|---|---|---|---|---|---|---|---|---|
| Relative activity (%) | 10 | 14 | 19 | 39 | 51 | 72 | 100 | 64 | 4 |

TABLE 8

| Temperature (°C.) | 4 | 30 | 40 | 50 | 55 | 60 |
|---|---|---|---|---|---|---|
| Residual activity (%) | 100 | 100 | 100 | 100 | 2 | 0 |

EXAMPLE 8

The isoelectric point of the purified esterase obtained in Example 2 was examined by means of electrophoresis under the following conditions:
- carrier: Ampholine (pH 3–10)
- density gradient of 0 to 50% sucrose
- voltage: at 400 V for 26 hours from the beginning and then at 800 V for 14 hours temperature: 2° C.
- 110 ml column was used.

As a result, the isoelectric point of said esterase was found to be 4.6±0.1

EXAMPLE 9

The purified esterase obtained in Example 2 (protein: 95 μg) was dialyzed against distilled water, and the dialyzed solution was evaporated to dryness. The residue was subjected to an amino acid sequencer. As a result, the amino acid sequence from N-terminal to 12th was found to be as follows:

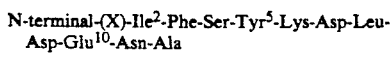

wherein X is an amino acid which has not yet been identified.

EXAMPLE 10

The effect of metal ions or known enzyme-inhibitors on the purified esterase obtained in Example 2 was investigated as follows:

1 mM each metal ion or 1 mM each inhibitor was added to the enzyme solution, and the enzyme activity was estimated in the same manner as described in Example 1.

The activity was shown as relative activity (%) (the activity estimated by no addition of metal ion or inhibitor=100).

(Results)

The results are shown in the following Tables 9 and 10.

TABLE 9

(The effect of metal ions)

| Metal ion (1 mM) | Relative activity (%) |
|---|---|
| no addition | 100 |
| $Co^{2+}$ | 0 |
| $Li^+$ | 143 |
| $Zn^{2+}$ | 29 |
| $Cu^{2+}$ | 57 |
| $Mg^{2+}$ | 123 |
| $Ni^{2+}$ | 0 |
| $Mn^{2+}$ | 11 |
| $Hg^{2+}$ | 86 |
| $Fe^{2+}$ | 0 |
| $Fe^{3+}$ | 0 |
| $Ca^{2+}$ | 285 |
| $Pb^{2+}$ | 86 |
| $K^+$ | 94 |

TABLE 10

(The effect of inhibitors)

| Inhibitors (1 mM) | Relative activity |
|---|---|
| without reagent | 100 |
| Ethylenediaminetetraacetic acid | 0 |
| p-Chloromercury benzoate | 86 |
| Sodium dodecyl sulfate | 157 |
| Phenylmethylsulfonyl fluoride | 100 |

EXAMPLE 11

12 liters of the supernatant obtained from the culture broth in the same manner as described in Example 1 were concentrated by using ultrafiltration membrane (SIP-3013, Asahi Chemical Industries Co., Ltd.). The concentrate was salted out with 35% saturated ammonium sulfate solution containing 10 mM Tris-HCl buffer (pH 7.5). The precipitate (esterase) was dissolved in 10 mM Tris-HCl buffer (pH 7.5). The solution was dialyzed and subjected to a column of an anion exchange resin (DEAE-TOYOPEAL 650M, manufactured by Toyo Soda Co., Ltd.) which was pre-equilibrated with the same buffer. The column was washed with 10 mM Tris-HCl buffer (pH 7.5). The elution of enzyme was carried out by a liner gradient of 0 to 0.8M sodium chloride solutions containing 10 mM Tris-HCl buffer (pH 7.5). Esterase was eluted with about 0.3M sodium chloride solutions containing 10 mM Tris-HCl buffer (pH 7.5). The active fractions were collected and dialyzed against 0.15M sodium chloride solution containing 10 mM Tris-HCl buffer (pH 7.5). The solution (101 ml) was concentrated to 8 ml by ultrafiltration (Diaflo ultrafilter PM-10, manufactured by Amicon Co., Ltd.). The concentrate was subjected to gel filtration of a molecular sieve resin (Sephacryl S-300 HR, manufactured by Pharmacia LKB Biotechnology) which was pre-equilibrated with the same buffer. The active fractions were collected and dialyzed against 2% saturated ammonium sulfate solution containing 10 mM Tris-HCl buffer (pH 7.5) and subjected to a column of a hydrophobic resin (Phenyl-TOYOPEAL 650M, manufactured by Toyo Soda Co., Ltd.) which was pre-equilibrated with the same buffer. The column was washed with the same buffer. Enzyme was eluted from the resin by a stepwise gradient of 2% to 0% saturated ammonium salfate solutions containing 10 mM Tris-HCl buffer (pH 7.5). 133 mg of purified esterase protein were obtained.

Physico-chemical properties and enzymatic characteristics of this purified esterase are identical to those obtained in Example 2.

The specific activities and yields of esterase obtained in each of the above-purification steps are shown in the following Table 11 (The enzyme activity was estimated in the same manner as described in Example 1 and the amount of protein was measured by Lowry method.). The esterase obtained above showed no protease activity when casein was used as the substrate.

All of purification steps above was carried out below 5° C.

TABLE 11

| Purification step | Total volume (ml) | Total protein (mg) | Total activity (units) | Specific activity (units/mg protein) | Yield (%) |
|---|---|---|---|---|---|
| Supernatant of culture | 12000 | 13900 | 1416000 | 102 | 100 |
| Concentration by UF membrane | 1000 | 1920 | 1343000 | 699 | 95 |
| 35% ammonium sulfate | 175 | 645 | 1269000 | 1967 | 90 |
| DEAE-TOYOPEAL 650M | 101 | 298 | 656000 | 2201 | 46 |
| Sephacryl S-300 HR | 45 | 194 | 590000 | 3041 | 42 |
| Phenyl-TOYOPEAL 650M | 18 | 133 | 414000 | 3113 | 29 |

EXAMPLE 12

The amino acid composition of purified esterase obtained in Example 11 was examined by using an amino acid analyzer under the following conditions.

Each enzyme solution in 6M hydrochloride (2.0 mg/ml) was sealed in a glass tube under vacuum and then hydrolyzed for 20, 40 or 70 hours at 110° C. The hydrolysate was evaporated to dryness under reduced pressure, dissolved in 0.02N hydrochloride solution and analyzed with an amino acid analyzer (Hitachi model L-8500). Cystein and cystine were determined as cysteic acid after performic acid oxidation of the sample according to the method of Moore[1]). Tryptophan was determined according to the method of Simpson et al.[2])

References
1) Moore, S. (1963) J. Biol. Chem. 238, 235-237.
2) Simpson, R. J., Neuberger, M. R., and Lin, T.-Y. (1976) J. Biol. Chem. 251, 1936-1940.

TABLE 12

| Amino acid | Residues/molecule[a] |
|---|---|
| Asx[b] | 89 |
| Thr[c] | 40 |
| Ser[c] | 43 |
| Glx[b] | 40 |
| Pro | 15 |
| Gly | 78 |
| Ala | 56 |
| Val | 28 |
| Ile | 31 |
| Leu | 58 |
| Tyr | 23 |
| Phe | 28 |
| Lys | 20 |
| His | 14 |
| Arg | 14 |
| Cys | 0-1 |
| Met | 2 |
| Trp | 7 |

[a] Based on a Molecular weight of 62,000.
[b] Sum of acid and amide forms.
[c] The serine and threonine values were obtained by extrapolation to time zero, assuming first-order decay.

EXAMPLE 13

The purified esterase obtained in Example 11 was dialyzed against water, and its calcium content was determined by using an atomic absoption spectrometry (Hitachi model Z-9000).

As a result, the calcium content in the purified esterase was one mole per an enzyme molecular mass of 62,000.

EXAMPLE 14

The substrate specificity of the purified esterase obtained in Example 11 on dimercaprol tributyrate was investigated in the same manner as described in Example 4.

The esterase showed the enzyme activity of $5.2 \times 10^5$ units/mg protein.

What is claimed is:

1. An essentially purified esterase derived from *Serratia marcescens* Sr41 (FERM BP-No. 487) having the following physico-chemical properties and enzymatic characteristics:
   (1) Activity: said esterase hydrolyzes an ester bond of organic carboxylates,
   (2) Substrate specificity: said esterase acts on alkyl esters of organic carboxylic acids, triglycerides or thiol esters,
   (3) Optimum pH: said esterase has an optimum pH of 7.5-9.0 when the hydrolysis is carried out using olive oil as the substrate,
   (4) pH stability: said esterase is stable at pH 5.0-9.0 when it is stored at 30° C. for one hour,
   (5) Optimum temperature: said esterase has an optimum temperature of 40°-50° C. when the hydrolysis is carried out using olive oil as the substrate,
   (6) Heat stability: said esterase is stable at a temperature of not higher than 50° C. when it is stored at pH 8.0 for 30 minutes,
   (7) Molecular weight: 62,000±2,000 (SDS-polyacrylamide gel electrophoresis),
   (8) Isoelectric point: 4.6±0.1,
   (9) Effect of metal ions: said esterase is activated in the presence of 1 mM calcium ion, and inhibited in the presence of 1 mM cobalt ion, nickel ion, iron ion or ethylenediaminetetraacetic acid.

* * * * *